United States Patent [19]

Garbe

[11] 3,941,283

[45] Mar. 2, 1976

[54] TIMED DROP APPLICATOR

[75] Inventor: Siegfried Garbe, Canton, Ohio

[73] Assignee: The Nilodor Company, Inc., North Canton, Ohio

[22] Filed: Dec. 14, 1973

[21] Appl. No.: 424,807

Related U.S. Application Data

[62] Division of Ser. No. 226,686, Feb. 16, 1972, Pat. No. 3,804,592.

[52] U.S. Cl. ............................. 222/187; 222/420
[51] Int. Cl.² ......................................... B67D 3/00
[58] Field of Search ............ 222/70, 187, 188, 420, 222/422; 239/49, 51, 326

[56] References Cited
UNITED STATES PATENTS

| 118,194 | 8/1871 | Burson | 222/187 |
|---|---|---|---|
| 762,316 | 6/1904 | Kelsey | 222/420 X |
| 1,171,737 | 2/1916 | Madigan | 239/49 |
| 2,406,746 | 9/1946 | Davis | 222/420 X |
| 2,520,056 | 8/1950 | Pozun | 222/187 X |

FOREIGN PATENTS OR APPLICATIONS

| 931,612 | 7/1963 | United Kingdom | 222/420 |
| 10,902 | 5/1908 | United Kingdom | 239/51 |

Primary Examiner—Stanley H. Tollberg
Assistant Examiner—Hadd Lane
Attorney, Agent, or Firm—Meyer, Tilberry & Body

[57] ABSTRACT

Arrangements are disclosed for dispensing liquid in droplet form at timed intervals from a receptacle defining a liquid reservoir. The receptacle includes openings at opposite ends thereof defined in part by integral externally threaded neck portions. One of the openings is employed to fill the receptacle and control the venting of the interior of the receptacle to atmosphere, thus to control stopping and starting of drop dispensing. The other of the openings is a dispensing opening including dispensing and timing means through which liquid in the receptacle is dispensed and by which the rate of drop dispensing is controlled. Absorbent material may be supported beneath the receptacle to receive drops dispensed therefrom to facilitate evaporation of the liquid, and fan means may be associated with the receptacle and absorbent material to further facilitate evaporation of the liquid and entrainment of odoriferous vapors from the liquid into the moving airstream caused by fan operation.

5 Claims, 10 Drawing Figures

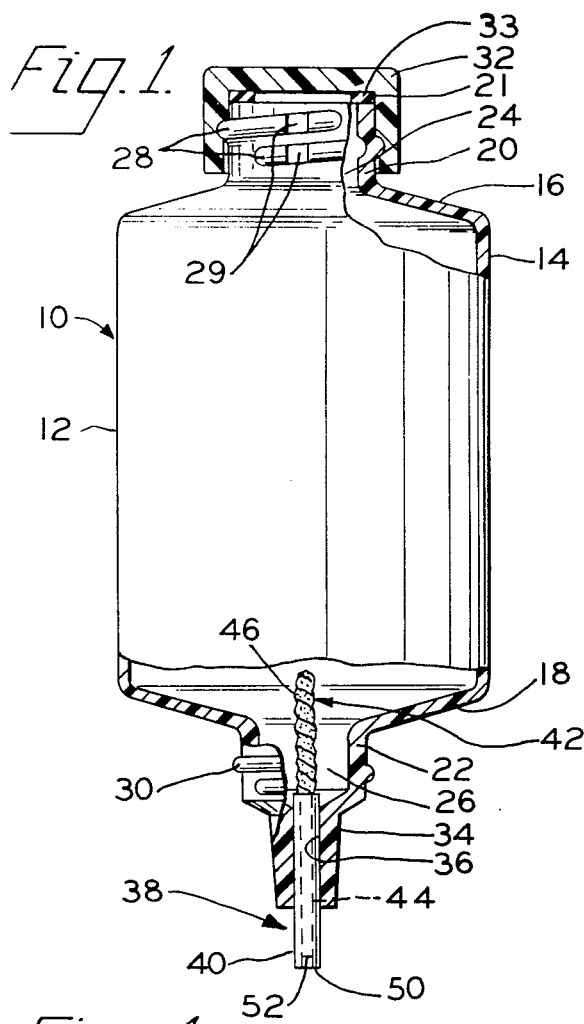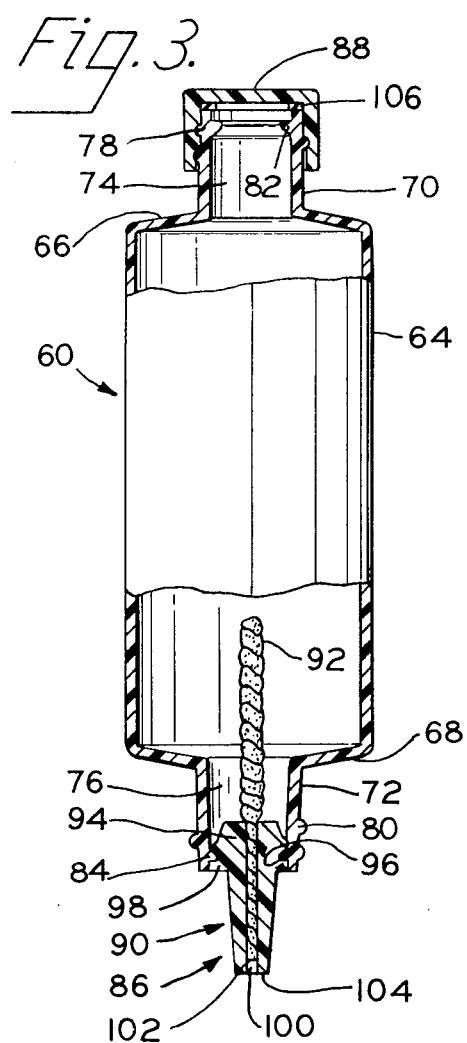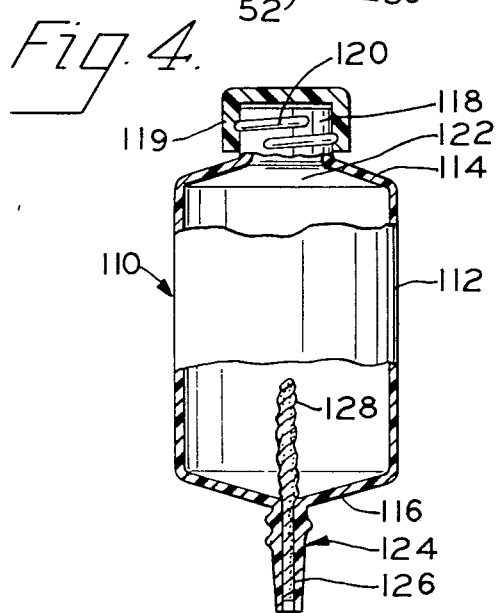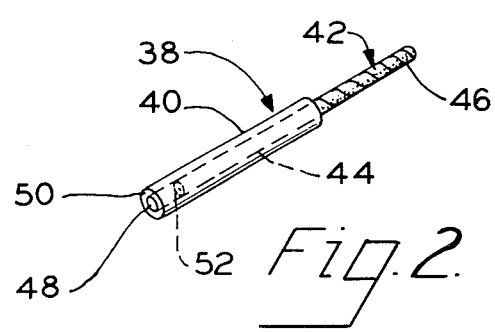

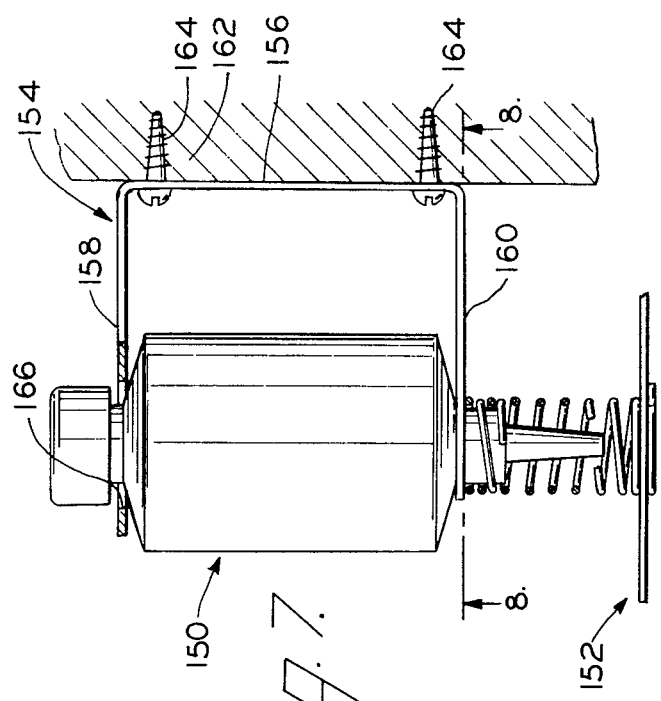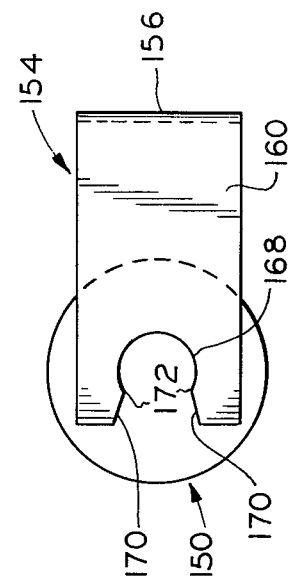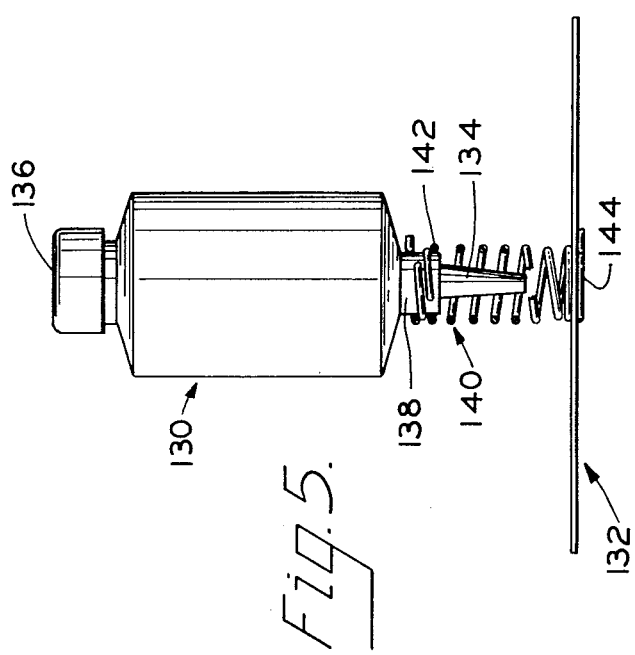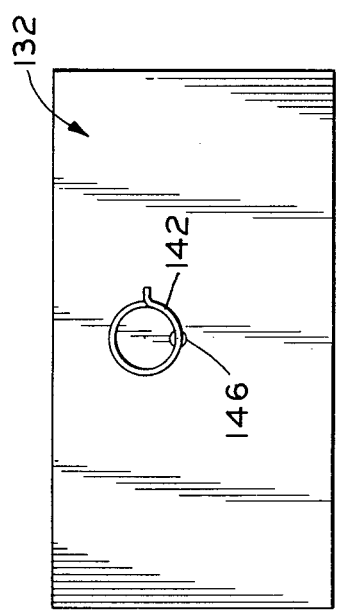

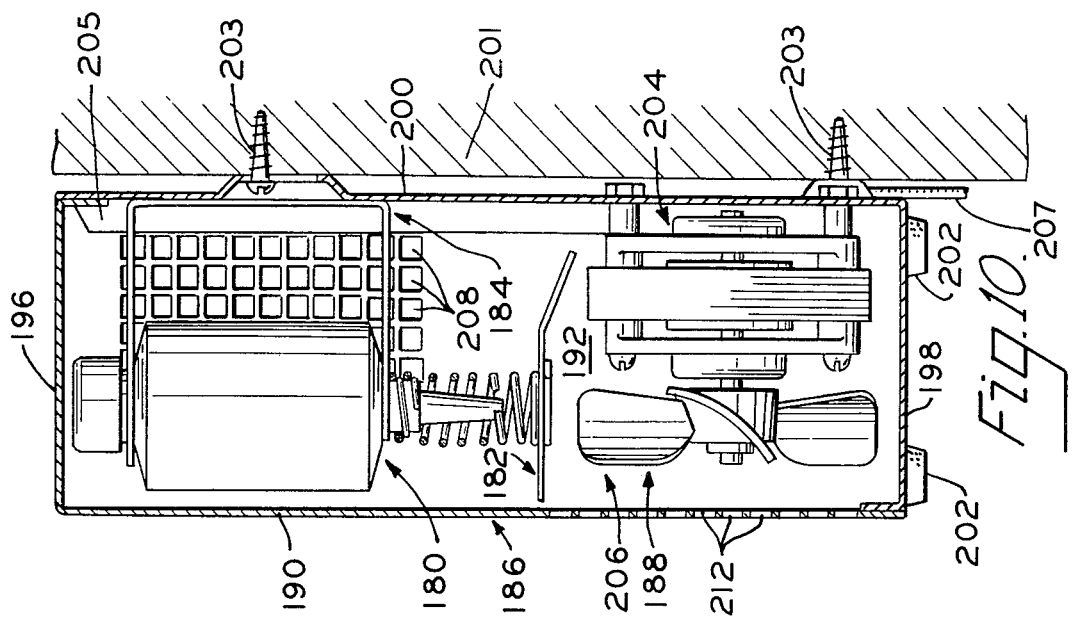
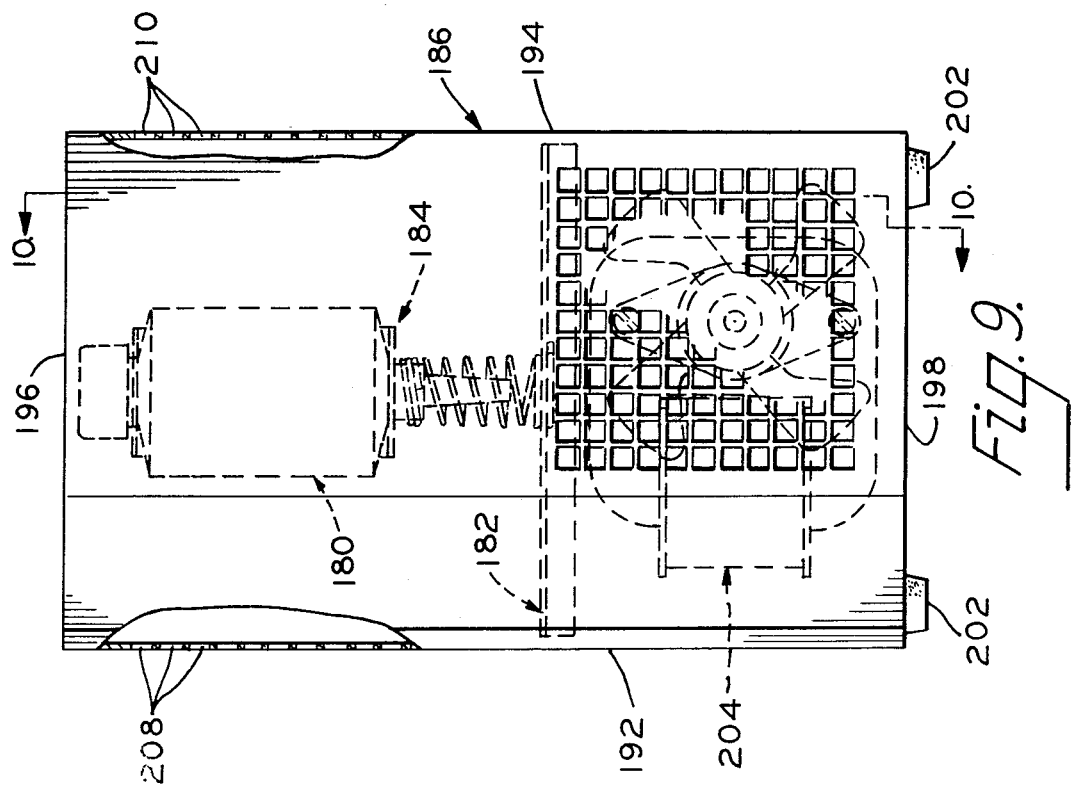

TIMED DROP APPLICATOR

This is a division of application Ser. No. 226,686 filed Feb. 16, 1972 now U.S. Pat. No. 3,804,592 of Apr. 16, 1974.

The present invention relates to the art of dispensing and, more particularly, to the dispensing of liquid in droplet form from a receptacle or reservoir.

In the dispensing of liquid in droplet form from a receptacle or reservoir it is often desirable to support the receptacle in a fixed disposition for the flow of liquid in droplet form therefrom to be achieved at timed intervals and over a considerable total period of time so that frequent observation of the dispensing operation is not required. For example, it is often desired to periodically dispense a drop of deodorizing liquid into a room or other enclosure or into sanitary equipment to maintain a pleasant aroma in the surrounding atmosphere. As another example, certain machinery and apparatus require periodic lubrication which advantageously can be provided at timed intervals by drop dispensing devices to eliminate the necessity that the machine or apparatus operator personally attend to the lubricating function each time it is required.

Drop applicator devices have, of course, been provided heretofore for the purpose of dispensing liquid in droplet form from a receptacle or reservoir. Generally, such devices include a reservoir or receptacle having an outlet opening provided with absorbent material such as a wick device to facilitate transfer of liquid from within the receptacle to a point of use exteriorly thereof. While such devices do operate to provide for the dispensing of liquid in droplet form they do not facilitate the economical production and use of such devices for purposes including those specifically mentioned hereinabove. The economical production and use of such devices is of extreme importance when it is considered that several hundred such units might be required to control an odor problem of a single establishment involved in, for example, the poultry industry. Thus, it is most desirable to provide a drop dispensing assembly which is economical to produce, is readily mountable in its use position and which, when mounted, can readily and easily be controlled to initiate or stop a dispensing operation and which facilitates replenishment of the liquid supply when necessary and modification of the drop dispensing rate with a minimum of effort on the part of the user and most often without separation or removal of the device from its support. Further, it is desirable, especially in conjunction with the dispensing of liquid deodorant, to enhance evaporation of dispensed liquid so that deodorant vapors are more rapidly entrained in the surrounding atmosphere.

In accordance with the present invention, the foregoing advantages are achieved by providing dispensing arrangements including receptacles having structural features which facilitate the filling thereof with liquid to be dispensed, the rate at which liquid droplets are dispensed therefrom, installation and support of the receptacles and dispersion of the liquid droplets dispensed therefrom. More particularly, with regard to one aspect of the present invention, a dispensing receptacle is provided having axially aligned openings therein each of which is defined in part by an externally threaded neck structure integral with the receptacle body. One of the openings is adapted to be employed to fill a receptacle with liquid and to receive a cap component operable to control the stopping and starting of drop dispensing from the receptacle. The other of the openings is a dispensing opening including timing and dispensing means which in certain embodiments is defined by removable insert means through which the liquid is dispensed in droplet form and by which the rate of drop dispensing is controlled. Advantageously, in the latter embodiments, a variety of inserts can be associated selectively with the dispensing opening, thus to provide for selectively choosing or changing the rate of droplet flow from the receptacle.

In accordance with another aspect of the present invention, the neck means at opposite ends of the receptacle facilitate the mounting of the receptacle relative to a support surface in a position of use, whereby stopping or starting of the drop dispensing operation can be achieved simply by manipulation of the cap component, and whereby replenishing of the liquid supply in the receptacle can be achieved simply by removal of the cap component. Therefore, both of these functions can be achieved without removal of the receptacle from its support component. Moreover, where the timing and dispensing means is defined by insert means, the latter can be changed most often while the receptacle is in the mounted disposition.

With regard to a narrower aspect of the present invention, the neck means associated with the dispensing outlet opening of the receptacle provides means by which absorbent material such as blotter paper or asbestos can be supported beneath the dispensing and timing means to receive and disburse liquid droplets dispensed from the receptacle. Dispersion of liquid droplets relative to the absorbent material advantageously facilitates evaporation of the liquid into the surrounding air. Still further, when the drop dispensing arrangement is employed in conjunction with a deoderizing function, the desired evaporation is advantageously supplemented by employing fan means to circulate ambient air relative to the absorbent material.

An outstanding object of the present invention is the provision of drop dispensing means in which the components thereof are economical to produce, lend to the ease of use of the arrangements and provide for more efficient control of drop dispensing functions than heretofore possible.

A further object is the provision of drop dispensing means of the above character including receptacle means having structures which facilitate mounting thereof in a use position and control of the starting and stopping of a dispensing operation when so mounted.

Another object is the provision of dispensing means of the above character wherein the structure of the receptacle means facilitates the use therewith of interchangeable dispensing and timing means through which the liquid is dispensed and by which the time interval between drops is controlled.

Yet another object of the present invention is the provision of dispensing arrangements of the above character wherein the structure of the receptacle means facilitates the support thereby of absorbent material onto which the liquid droplets are dispensed thus to facilitate evaporation of the liquid dispensed.

Still a further object of the present invention is the provision of dispensing arrangements of the above character in which fan means is employed to circulate ambient air past the absorbent material to facilitate entrainment of liquid vapor into the ambient air.

These objects and others will in part be obvious and in part more fully pointed out hereinafter in conjunction with the description of the drawing in which:

FIG. 1 is an elevation view, partially in section, of drop dispensing receptacle means made in accordance with the present invention;

FIG. 2 is a perspective view of timing and dispensing insert means employed with the receptacle means of FIG. 1;

FIG. 3 is an elevation view, partially in section, of another embodiment of receptacle means within the present invention.

FIG. 4 is an elevation view, partially in section, of yet another embodiment of receptacle means within the present invention;

FIG. 5 is a front elevation view of receptacle means made in accordance with the present invention and illustrating a sheet of absorbent material supported thereby adjacent the dispensing outlet;

FIG. 6 is a plan view of the absorbent material and means for attaching the material to a receptacle.

FIG. 7 is a side elevation view of the receptacle means similar to that illustrated in FIG. 5 and further illustrates the receptacle means in the mounted disposition thereof;

FIG. 8 is a bottom view of the receptacle and mounting arrangement illustrated in FIG. 7 taken along line 8—8 in FIG. 7;

FIG. 9 is a front elevation view illustrating the receptacle of FIG. 7 supported within an enclosure together with means for circulating ambient air through the enclosure; and FIG. 10 is a side elevation view, in section, of the arrangement illustrated in FIG. 9, the section being taken along line 10—10 in FIG. 9.

Referring now to the drawings in greater detail wherein the showings are for the purpose of illustrating preferred embodiments of the present invention only and not for the purpose of limiting the same, dispensing receptacle means 10 is illustrated in FIG. 1 which is comprised of a cylindrical body portion 12 defined by side wall means 14 and end wall means 16 and 18 at opposite ends of side wall means 14. The receptacle means 10 is further defined by cylindrical neck means 20 at one end thereof and cylindrical neck means 22 at the other end thereof. Preferably, end wall means 16 and 18 are integral with side wall means 14, and neck means 20 and 22 are integral with end wall means 16 and 18, respectively, whereby an integral receptacle unit is defined thereby. The receptacle unit may be produced from any suitable material, preferably a plastic material, and in the preferred embodiment the receptacle unit is produced from high density polyethylene. Moreover, the receptacle unit can be produced in any desired manner such as, for example, by blow molding.

Receptacle means 10 has opening means 24 in one end thereof defined in part by neck means 20 and opening means 26 in the other end thereof defined in part by neck means 22. Further, neck means 20 is provided with integral external thread means 28 and neck means 22 is provided with integral external thread means 30. Opening means 24 serves as an inlet opening through which liquid to be dispensed can be introduced into the receptacle means. Further, the latter opening is adapted to be closed by closure or cap means 32 which is internally threaded for cooperable threaded engagement with thread means 28. Cap means 32, in a manner set forth more fully hereinafter, also defines means to stop and start the dispensing of liquid from receptacle means 10.

Neck means 22 includes a restricted outer end portion 34 which defines a bore 36 which is substantially uniform in cross-sectional dimension along the length thereof. Bore 36 is adapted to removably receive dispensing and timing insert means 38. As best illustrated in FIG. 2 of the drawing, insert means 38 is comprised of a sleeve component 40 and wick means 42 having one end 44 thereof disposed in sleeve 40 and the other end 46 thereof extending from the corresponding end of the sleeve. Wick means 42 may be defined by any suitable material and, preferably, is defined by cotton fibers interrelated with wire core means in a manner similar to that of a pipe cleaner. Sleeve 40 is substantially uniform in external cross-sectional contour along its length and is adapted to be tightly received in neck bore 36 so as to prevent unintended displacement of the sleeve relative to the bore and to seal the area between the surface of the bore and the external surface of the sleeve. Further, wick means 42 and bore 48 of sleeve 40 are relatively dimensioned so that the end 44 of the wick means which is disposed in the sleeve is radially compressed thereby. The extent to which wick means 42 is radially compressed determines the rate of flow of liquid along the wick means to outlet end 50 of sleeve 40. Accordingly, by having sleeve means 40 removably associated with neck bore 36 it is possible to provide a plurality of dispensing and timing insert means each having a sleeve 40 and wick means 42 and wherein the internal dimension of the sleeves are different to provide for different degrees of compression of the wick means, whereby different rates of drop dispensing are obtained.

Sleeve 40 of dispensing and timing means 38 can be of any suitable material such as metal or plastic and, preferably, is cylindrical in cross-sectional configuration. Further, it is preferred that the end 52 of wick means 42 may be axially spaced inwardly of end 50 of sleeve 40 so that the end of the wick means adjacent the outlet end of the sleeve is not directly exposed to ambient air. This feature advantageously prevents end 52 of wick means 42 from becoming clogged during use such as would result from exposure of the wet end to ambient air if end 52 were disposed axially outwardly from sleeve end 50. Further, in this regard, it will be appreciated that the liquid being dispensed saturates the wick means whereby the exposed end of the wick means would be wet during the period of time between the dispensing of successive drops. Exposure of the wet wick to ambient air can, depending on the liquid being dispensed, cause a certain amount of the material to dry and adhere to the wick whereby eventually, the wick becomes clogged and the dispensing function is either completely interrupted or is otherwise undesirably altered. By providing for end 52 of the wick to be spaced inwardly from end 50 of sleeve 40 such clogging is advantageously avoided even when the time period between the dispensing of successive drops is of considerable duration.

In operation of the dispensing unit illustrated in FIG. 1, cap means 32 is removed and the receptacle is filled to a desired level with the liquid to be dispensed therefrom. Cap means 32 is then replaced and is screwed into tight engagement with end face 21 of neck means 20. This tightly seals opening 24 against ingress of ambient air therethrough into the receptacle. Such sealing can be further assured, if desired, by the provision of a sealing gasket 33 within cap means 32. When cap means 32 has been screwed into tight engagement with the neck means 20, the receptacle unit can be disposed in its use position with neck means 22 extending downwardly and, because of the sealed relationship, dispensing of drops from the receptacle unit will not take place. A dispensing operation can be initiated by unscrewing cap means 32 to break the seal, whereby ambient air is vented into the receptacle behind the liquid therein. To facilitate such venting, thread means 28 may be interrupted such as is indicated at 29. The unscrewing of cap means 32 about one-half turn is generally adequate to provide the desired venting, and dispensing of liquid in drop form begins when the cap seal is broken. From that point on, liquid drops are dispensed from the receptacle at timed intervals determined, as mentioned hereinabove, by the relative dimensions of wick means 42 and bore 48 in sleeve 40. When it is desired to stop the dispensing function, it is only necessary to screw cap means 32 into sealing engagement with neck means 20. Further, when it is desired to replenish the liquid supply in the receptacle, it is only necessary to remove cap means 32 and introduce liquid into the receptacle through opening 24.

FIG. 3 illustrates another embodiment of dispensing receptacle means made in accordance with the present invention. In this respect, receptacle means 60 of suitable plastic material, preferably polyethylene, is illustrated which is comprised of cylindrical body portion 64 and end wall means 66 and 68 at opposite ends of body portion 64. Cylindrical neck means 70 extends axially outwardly from end wall means 66 and cylindrical neck means 72 extends axially outwardly from end wall means 68. As in the embodiment illustrated in FIG. 1, end walls 66 and 68 preferably are integral with the corresponding ends of body portion 64, and neck means 70 and 72 preferably are integral with the corresponding end walls 66 and 68.

Receptacle means 60 has an opening 74 at one end thereof defined in part by neck means 70 and an opening 76 in the other end thereof defined in part by neck means 72. In this embodiment, openings 74 and 76 are substantially the same size and neck means 70 and 72 are substantially identical in diameter and in axial length relative to the corresponding end wall of the receptacle. Moreover, neck means 70 is provided with integral external thread means 78 and neck means 72 is provided with integral external thread means 80. Thread means 78 and 80 are also substantially identical. Further, neck means 70 and 72 are each provided with radially inwardly projecting annular lip means 82 and 84, respectively, for the purpose set forth more fully hereinafter. Thus, it will be appreciated that the receptacle means is provided with substantially identical opening and neck means at the opposite ends thereof.

Receptacle means 60 further includes removable dispensing and timing means 86 at one end thereof and cap means 88 at the other end thereof. Dispensing and timing means 86, in this embodiment, is defined by sleeve means 90 and wick means 92. Sleeve means 90 is in the form of a plug 94 adapted to be releasably interengaged with lip means 84 of neck means 72. In this respect, plug 94 includes an annular recess 96 adapted to receive lip means 84. Recess 96 is defined in part by a radially outwardly extending flange 98 adapted to seat within the outer end of neck means 72 and against lip means 84. The configurations of recess 96, flange 98 and lip means 84 and the dimensional relationship therebetween is such that plug 94 is adapted to be snapped into place within neck means 72 in a manner whereby it is releasably retained therein and the engaging surfaces of the plug and neck means provide a seal against leakage of liquid therebetween. Plug 94 includes an axially extending bore 100 having a substantially uniform cross-sectional dimension along the length thereof, and the portion of wick means 92 disposed within bore 100 is radially compressed therein in a manner similar to that hereinbefore described with regard to the embodiment of FIGS. 1 and 2. Accordingly, the relative dimensions of bore 100 and wick means 92 determine the rate at which liquid drops are dispensed from the receptacle. Wick means 92 preferably is a wire cored fiber material, and it will be appreciated that the wire core advantageously provides rigidity for the wick means to facilitate its axial introduction into bore 100. Further, for reasons hereinbefore set forth, end 102 of wick means 92 preferably is spaced inwardly from outlet 104 of plug 94.

Cap means 88 is similar to cap means 32 described with reference to the embodiment illustrated in FIG. 1. In this respect, the cap may be provided with an internal sealing gasket 106 to facilitate sealing engagement thereof with the outer end of neck means 70. Further, thread means 78 and 80 at opposite ends of the receptacle may be interrupted in the manner described hereinabove to provide a vent passageway thereacross.

While dispensing and timing means 86 is illustrated as being interengaged with neck means 72, and cap means 88 is illustrated as being interengaged with neck means 70, it will be appreciated that by providing the receptacle means with identical opening and neck means at opposite ends thereof the dispensing and timing means and the cap means can advantageously be selectively employed at either end of the receptacle means. Moreover, the identical end structure feature provides for cap means such as cap means 88 to be provided on both ends of the receptacle to facilitate shipment or storage of the receptacle with liquid therein, if so desired. Accordingly, when it is desired to use the receptacle it is only necessary to remove one or the other of the cap means and insert a dispensing and timing assembly into the corresponding neck means. The cap means at the other end of the receptacle then provides for controlling the starting and stopping of a dispensing operation in the manner hereinabove described with regard to the embodiment of FIG. 1 and for replenishing the liquid supply when necessary.

FIG. 4 illustrates yet another embodiment of dispensing means in accordance with the present invention. In this respect, receptacle means 110 is illustrated which is comprised of a body portion 112 and end wall means 114 and 116 at opposite ends of body portion 112. Neck means 118 having integral external thread means 120 thereon extends axially from end wall means 114 to define an opening 122 in the corresponding end of the receptacle means. Neck means 118 is adapted to receive cap means of the character illustrated and described hereinbefore with regard to the embodiments of FIGS. 1 and 3. Neck means 124 extends integrally from wall means 116 at the opposite end of body portion 112. In this embodiment, neck means 124 defines an opening 126 which is substantially uniform in cross-sectional dimension along the length of neck means 124. Accordingly, opening 126 defines a bore adapted to receive wick means 128 which is similar in structure to the wick means described hereinabove. In this instance, neck means 124 and wick means 128 define dispensing and timing means which are integral with the receptacle and which function in a manner similar to the dispensing and timing means described hereinabove with regard to the embodiments of FIGS. 1 and 3. In this respect, the relative dimensions of opening 126 and wick means 128 determines the extent to which the wick means is radially compressed within the opening and thus the time interval between the dispensing of successive drops of liquid from the receptacle. Stopping and starting of a dispensing operation and the filling or replenishing of the receptacle with liquid is achieved by cap means 119, illustrated by broken lines, adapted to be associated with neck means 118 in a manner similar to that described hereinabove with regard to the earlier embodiments. Receptacle means 110, as in the earlier embodiments is produced, preferably, from high density polyethylene.

Another feature of the present invention is illustrated in FIGS. 5 and 6 of the drawing. In this respect, drop dispensing receptacle means 130 is illustrated as having absorbent means 132 supported relative thereto and in a position to receive drops dispensed from the outlet end 134 of the receptacle means. Receptacle means 130 may be any one of the receptacle means described hereinabove and, in this respect, includes cap means 136 at one end thereof and externally threaded neck means 138 at the end thereof from which liquid droplets are to be dispensed. Absorbent means 132 may be of any desired configuration and material and, preferably, is in the form of a sheet of heavy gauge blotter paper or asbestos sheeting. Further, the absorbent material may be supported relative to the receptacle means in any desired manner and, preferably, is suspended from neck means 138 by coil spring means 140 having one end 142 thereof interengaged with threaded neck means 138 of the receptacle and the other end 144 thereof engaged under the sheet material. For the latter purpose, the sheet of absorbent material is provided with an opening 146 positioned generally centrally thereof to facilitate threading of the corresponding end convolution of the spring through the sheet material. The thread on neck 138 of the receptacle advantageously provides for assembling and retaining spring 140 in place relative to the receptacle and, accordingly, it will be appreciated that the threads on the necks of all of the embodiments of receptacles herein described facilitate the attachment of absorbent material to the corresponding receptacle unit. The absorbent material advantageously provides for dispersing or spreading a liquid drop dispensed thereonto, whereby evaporation of the liquid is enhanced. This feature is of particular importance when the drop dispensing means is employed to provide a deoderizing function in an enclosure such as a room. Moreover, suspending of the absorbent material at a point generally centrally thereof is preferred in that such support advantageously prevents upward distortion of the center area of the material such as would occur if the material were perimetrally supported. Such upward distortion of the absorbent material undesirably provides for drops to collect along the peripheral edges thereof.

FIGS. 7 and 8 of the drawing illustrate yet another feature of the present invention. In this respect, receptacle means 150 is illustrated having absorbent material 152 supported relative to the outlet end thereof in a manner similar to that illustrated in FIGS. 5 and 6 of the drawing. In the embodiment of FIGS. 7 and 8, the receptacle means is supported in its use position by bracket means 154 in the form of a C-shaped bracket having a base portion 156 and leg portions 158 and 160 extending from opposite ends of base portion 156. Base portion 156 is adapted to be interconnected with support means 162 in any suitable manner such as, for example, by means of threaded fasteners 164. It will be appreciated, of course, that other fastening means, such as magnetic holding means for example, could readily be employed. Upper leg 158 of bracket means 154 is provided with a cylindrical opening 166 through which the cap means and corresponding neck means of the receptacle is adapted to project. Bottom leg means 160 is provided with an arcuate recess 168 having an entrance thereinto from the front end of leg 160, which entrance is defined by outwardly diverging side portions 170. Recess 168 has an arcuate contour for an extent of more than 180° whereby a throat is defined by the space between points 172 at which the arcuate line of the recess engages the corresponding side portion 170. The diameter of the arcuate portion of recess 168 is substantially equal to the diameter of the neck means of the receptacle adjacent the corresponding end wall of the receptacle, and the distance between points 172 is slightly less than the diameter of the neck means. Thus a throat area or restriction is defined past which the neck means must be forced to achieve entry of the neck means into recess 168. Accordingly, it will be appreciated that this structure provides for snap fitting the corresponding neck means of the receptacle into place relative to the bracket means. The bracket and receptacle structures accordingly cooperate to provide for absorbent means 152 to be applied to the neck means of the receptacle, for the receptacle to be filled and for the mounting of the receptacle unit in its use position to be achieved simply by inserting the cap end of the receptacle upwardly through opening 166 and then pressing the neck means at the lower end of the receptacle into position in recess 168. Further, the structural relationship between the receptacle and bracket provides for the cap means at the upper end of the receptacle to be exposed when the receptacle is in its mounted position whereby stopping and starting of a dispensing function and the replenishing of the receptacle with liquid is readily achieved simply by manipulating or removing the cap means and without disturbing the mounted disposition of the receptacle unit. Moreover, the timing and dispensing insert means, where applicable, can readily be changed without removal of the receptacle from the bracket.

FIGS. 9 and 10 of the drawing illustrate yet another embodiment of the present invention wherein receptacle means 180 which may be of the character of any of the receptacle means hereinabove described is supported together with absorbent means 182 by bracket means 184 within housing and support means including housing or enclosure means 186. The use of housing means is advantageous in situations where it is desired to provide for the dispensing assembly to present an attractive appearance. Further, the housing and support means provides for the dispenser assembly to be provided with air circulating means such as fan means 188 which is disposed in the housing or enclosure means and is operable to draw ambient air into the housing means and past absorbent means 182 and thence outwardly into the room or enclosure in which the assembly is disposed. The housing may be of any suitable structural configuration and material and, preferably, includes front wall means 190, sidewall means 192 and 194, top wall means 196 and bottom wall means 198. Wall means 190, 192, 194, 196 and 198 preferably are suitably interconnected with one another to define a unitary structure. Further, the housing and support means includes support means which, in the embodiment illustrated, is in the form of support plate means 200 which is adapted to be mounted on support surface means 201, such as a wall or the like, by means such as threaded fasteners 203. Moreover, bottom wall means 198 may be provided with support means such as is defined by foot components 202 to provide for the assembly to rest on a horizontal surface as opposed to being mounted on a vertical surface. Preferably, bracket means 184 and fan means 188 are suitably attached to support plate means 200, and the latter is provided with flange means 205 to removably support the unitary housing or enclosure structure. It will be appreciated, however, that bracket means 184 may be attached to support means 201 in a manner similar to that described in conjunction with the embodiment of FIGS. 7 and 8, and that the housing means may be separately attached to support means 201 or suitably supported by the bracket means. Further, it will be appreciated, that the fan means may also be separately attached to support means 201 if so desired. In any event, the fan means will be positioned relative to the dispensing unit in a manner whereby operation of the fan means causes ambient air to flow past absorbent means 182.

Fan means 188 may be of any suitable design and structure and in the embodiment illustrated includes electric motor means 204 adapted to be connected by means of lead 207 to any suitable electric power supply, not illustrated. Fan means 188 further includes blade means 206 driven by the motor to cause air circulation. Preferably, ambient air is drawn into the housing in a direction which is lateral to front wall means 90 and is exhausted from the housing through the front wall. In this respect, side wall means 192 and 194 may be provided with a plurality of suitable air inlet openings 208 and 210, respectively, and front wall 190 may be provided with a plurality of air outlet openings 212 in front of blade means 206. It will be appreciated, of course, that wall means 196 could also be provided with air inlet openings and that such openings could function alone or together with openings 208 and 210 in wall means 192 and 194. Still further, it will be appreciated that air circulating means 188 could be positioned relative to receptacle means 180 and the inlet and outlet openings in the housing in a manner whereby the fan would blow air past the absorbent material as opposed to inducing air flow therepast in the manner illustrated in FIGS. 9 and 10. The desired flow pattern for air circulated by the blower advantageously provides for deodorant vapors rising from the surface of absorbent means 182 to be entrained in the airstream and carried thereby in a direction which is transverse to that of the incoming air, thus to create a circulating air pattern to avoid the intake of air which has recently been treated. This air circulating effect may be supplemented by providing for the inlet openings 208 and 210 to be disposed adjacent the upper end of the housing and for the outlet openings 212 to be disposed adjacent the lower end of the housing, whereby maximum separation of the inlet and outlet openings relative to the housing is achieved.

As many possible embodiments of the present invention may be made and as many possible changes may be made in the embodiments herein illustrated, it is to be distinctly understood that the foregoing description of preferred embodiments is to be interpreted merely as illustrative of the present invention and not as a limitation.

I claim:

1. A liquid drop dispenser comprising a non-metallic receptacle for liquid to be dispensed and having a body portion and opposite ends integral with said body portion, said receptacle including first and second axially aligned openings in said opposite ends defined respectively by first and second neck means integral with and extending axially outwardly from the corresponding end, drop dispensing means including constricted wick means associated with said first opening for dispensing liquid in droplet form from said receptacle at predetermined fixed time intervals, said drop dispensing means being operable to dispense drops at said fixed time intervals whenever the interior of said receptacle is vented to atmosphere, said wick means being radially constricted along a length thereof to alone provide said predetermined fixed time interval between drops dispensed when said interior is vented to atmosphere, a closure cap on said second neck means, said closure cap and second neck means being cooperably threaded for said second neck means to support said closure cap for displacement relative thereto, said closure cap being selectively displaceable between said first and second positions on said second neck means, said closure cap in said first position sealingly engaging said second neck means to seal the interior of said receptacle relative to atmosphere to prevent dispensing, said closure cap and second neck means in said second closure cap position venting said interior to atmosphere to achieve dispensing at said fixed time intervals, and said closure cap being removable from said second neck means to facilitate introducing liquid into said receptacle through said second opening.

2. The drop dispenser according to claim 1, wherein said drop dispensing means includes a sleeve releasably interrelated with said first opening, said sleeve having a bore of uniform cross section along its length, and said wick means being radially compressed within said bore and cooperable therewith to provide said fixed time intervals.

3. The drop dispenser according to claim 1, wherein said first opening includes a cylindrical bore in said first neck means and of uniform diameter along its length, said wick means being radially compressed within said bore and cooperable therewith to provide said fixed time intervals.

4. A liquid drop dispenser comprising a nonmetallic receptacle for liquid to be dispensed and having a body portion and opposite ends integral with said body portion, said receptacle including first and second axially aligned openings in said opposite ends defined respectively by first and second neck means integral with and extending axially outwardly from the corresponding end, drop dispensing means including constricted wick means associated with said first opening for dispensing liquid in droplet form from said receptacle at predetermined fixed time intervals, said drop dispensing means being operable only when the interior of said receptacle is vented to atmosphere and said timed intervals being determined by said constricted wick means alone, a closure cap on said second neck means, said closure cap and second neck means being cooperably threaded for said second neck means to support said closure cap for displacement relative thereto, said closure cap being selectively displaceable between first and second positions on said second neck means, said closure cap in said first position sealingly engaging said second neck means to seal the interior of said receptacle relative to atmosphere to prevent dispensing, said closure cap and second neck means in said second closure cap position venting said interior to atmosphere to achieve dispensing, said closure cap being removable from said second neck means to facilitate introducing liquid into said receptacle through said second opening, said drop dispensing means including a sleeve releaseably interrelated with said first opening, said sleeve having a bore of uniform cross section along its length, said wick means being radially compressed within said bore and cooperable therewith to provide said fixed time intervals, said first and second neck means being structurally identical, and said closure cap and said sleeve being adapted to be selectively associated with either of said first and second neck means.

5. The drop dispenser according to claim 4, wherein said sleeve of said drop dispensing means and the inner surface of said first neck means defining said first opening include cooperable interengaging rib and groove means.

* * * * *